Figure 1:
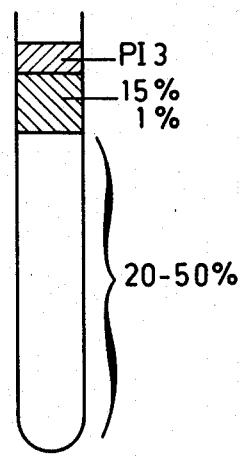

United States Patent [19]

Simons et al.

[11] 4,356,169

[45] Oct. 26, 1982

[54] METHOD OF PREPARING AN IMMUNOGENIC MEMBRANE PROTEIN AGGREGATE OF INFLUENZA AND PARAINFLUENZA VIRUSES AND RHABDOVIRUSES

[75] Inventors: Kai Simons; Ari Helenius, both of Heidelberg, Fed. Rep. of Germany

[73] Assignee: Europaisches Laboratorium Fur, Heidelberg, Fed. Rep. of Germany

[21] Appl. No.: 248,785

[22] Filed: Mar. 30, 1981

[30] Foreign Application Priority Data

Apr. 14, 1980 [DE] Fed. Rep. of Germany ....... 3014189

[51] Int. Cl.³ ................. A61K 39/12; A61K 39/205; A61K 39/155; A61K 39/145
[52] U.S. Cl. .................................. 424/89; 435/235; 435/236; 435/239
[58] Field of Search ................. 424/89; 435/235, 236, 435/239

[56] References Cited

U.S. PATENT DOCUMENTS

| | | | |
|---|---|---|---|
| 3,519,400 | 7/1970 | Anderson | 435/239 |
| 3,962,421 | 6/1976 | Neurath | 424/89 |
| 3,973,000 | 8/1976 | Lavender | 435/239 |
| 4,029,763 | 6/1977 | Kilbourne | 424/89 |
| 4,064,232 | 12/1977 | Bachmayer et al. | 424/89 |
| 4,113,712 | 9/1978 | Funakushi | 424/89 X |
| 4,140,762 | 2/1979 | Bachmayer et al. | 424/89 |
| 4,206,014 | 6/1980 | Reichert et al. | 424/89 |
| 4,255,520 | 3/1981 | Schell | 424/89 |

*Primary Examiner*—Shep K. Rose
*Attorney, Agent, or Firm*—Felfe & Lynch

[57] ABSTRACT

The invention relates to a method of preparing immunogenically active, lipid and detergent free soluble aggregates of amphiphilic membrane proteins of influenza and parainfluenza viruses and rhabdoviruses.

8 Claims, 3 Drawing Figures

METHOD OF PREPARING AN IMMUNOGENIC MEMBRANE PROTEIN AGGREGATE OF INFLUENZA AND PARAINFLUENZA VIRUSES AND RHABDOVIRUSES

The inocula or the vaccines, as the case may be, which are available against many coated viruses causing diseases in human beings and animals, are not only unsatisfactorily active, but also they are not free of undesirable side effects. Developments in the immunological field are moving mainly in two directions. In the one case, one tries to use living, attenuated viruses as inoculants, and in the other one seeks to develop improved inoculants on the basis of virus subunits (subunit vaccines). In the case of the attenuated live viruses, the difficulty occurs that strains must be found which are at once safe and effective. Serious side effects may develop slowly and are difficult to detect. The surface glycoproteins of coated viruses are considered to be the chief antigens in the virus particles, which induce the protective immune response against infection. An effective subunit vaccine against such a virus should therefore be a preparation from the antigens of the surface of the virus, from which the other components of the virus have been separated. Experiments with such inoculants, however, have produced no more than dubious results. For example, a series of subunit vaccines has been prepared, but these are at best only partially effective in the prevention of disease, and they have not been able to inhibit the spread of influenza epidemics. One chief difficulty is that the antigens of the virus surface are integral membrane proteins. Before they can be separated from the other virus proteins and the virus genome, the proteins must be solubilized. The method most used for the solubilization of such proteins consists in using detergents. These, however, bind the proteins and can change their antigenic potency. If the concentration of the detergent is reduced, the protein can precipitate or can adhere to available surfaces by hydrophobic interaction. The effectiveness of such detergent-solubilized virus surface antigens as inoculants is therefore very difficult to predict.

German Offenlegungsschrift No. 2,829,089 has disclosed a method of the kind described above, for the preparation of parainfluenza virus, in which the immunogenically active glycoprotein component is selectively extracted with a cationic detergent. It becomes possible in this manner to prevent undesired side effects and complications caused by other virus components, especially the genome. The immunogenic effectiveness of the subunit vaccines thus obtained, however, leaves much to be desired.

It is therefore the object of the invention to create subunit vaccines against diseases caused by influenza viruses, parainfluenza viruses or rhabdoviruses, which will not provoke the undesirable side effects produced by other virus components, but on the other hand will have a very high immunogenic activity.

This problem is solved in accordance with the invention by a method of preparing immunogenically active, lipid-free and detergent-free, soluble aggregates of amphiphilic membrane proteins of parainfluenza and influenza viruses and rhabdoviruses by extraction of the membrane with surface active agents, which is characterized by the fact that the virus is mixed with a nonionic or bile acid detergent, the mixture in a buffered aqueous salt solution is layered over a detergent-free sugar gradient which in turn is overlayered with a sugar solution containing detergent, and is centrifuged at at least 150,000 g, the protein-containing fraction is isolated and dialyzed against buffer solution, and the protein micelle solution obtained is lyophilized.

The protein micelles obtainable in accordance with the invention consist of aggregates of the immunogenically active spike proteins having a rosette-like structure. The rosettes are visible in the electron microscope. Their very high immunogenic activity is attributed to the fact that in these rosettes the hydrophobic ends of the spike proteins cluster together and the hydrophilic and immunogenic ends are pointed outwardly and they have a concentration of immunogenic points which is greater than the concentration of the intact virus.

For the performance of the process of the invention, first the virus is obtained conventionally from a suitable tissue, concentrated, for example by hollow fiber dialysis, and isolated, for example by gradient centrifugation. The purified virus is then mixed with the nonionic detergent or the detergent based on a bile acid, which is used in an excess amount. Typical examples of suitable nonionic detergents are the polyglycols esters and ethers with aliphatic and araliphatic acids and alcohols. Especially preferred is Triton X100 (octylphenol ether of polyethylene oxide). Typical examples of suitable bile acid detergents are deoxycholate and cholate.

As mentioned above, the detergent is used in an excess above the amount of the virus. It is desirable to mix the virus and detergent in a weight ratio of from 1:3 to 1:10.

The virus and detergent are combined in buffered salt solution. The molarity of the salt solution is between 0.02 and 0.5 M, preferably between 0.05 and 0.25 M. Especially preferred are 0.1 to 0.2 M. Sodium chloride is preferred as the salt, although other salts can be used, especially those having alkali (including ammonium) and alkaline earth ions, as well as the strong mineral acids and organic acids such as acetic acid, trichloroacetic acid, formic acid and oxalic acid.

All of the substances which buffer in the above-stated pH range are suitable for use as buffers. Especially good results are obtained with tris buffers.

The virus-detergent mixture prepared as described above is layered over a sugar gradient over which lies a layer of a detergent-containing solution of the same sugar, and centrifuged at not less than 150,000 g. The sugar gradient is detergent-free. Saccharose is preferred as the sugar for the gradient, but other disaccharides and monosaccharides can be used, as can glycerin, but tetroses and pentoses can also be used.

The sugar concentration in the gradient can best have a value of 15 to 25% as the initial concentration and 45 to 60% as the final concentration. The gradient can consist, for example, of an upper layer of 15 to 25% sugar content and a lower layer of 45 to 60% sugar content. However, there can also be a plurality of layers in which the differences in concentration between the individual layers are accordingly smaller.

The sugar gradient supports a layer consisting of a solution of the sugar which contains detergent. The concentration of the detergent, which is the same as it is in the virus-detergent mixture, is best between 0.25 and 3%, preferably between 0.75 and 1.5%. The sugar concentration can be equal to or lower than it is in the top layer of the gradient.

The vaccine obtained in accordance with the invention from spike protein aggregates of influenza or parainfluenza viruses is best dissolved in an appropriate solvent, such as physiological sodium chloride solution for example, for administration. 0.1 M NaCl solution, pH 7.2 to 7.6, is preferred. The pH has been adjusted with 0.05 M tris-HCl, but other buffers can also be used. Conventional adjuvants can also be added to the solution thus obtained, for the purpose of increasing its activity. Of these, Freund's incomplete adjuvant (consists of 20% Falba in Bayol F) is preferred. It is possible by the addition of adjuvant to reduce the amount of influenza micelles required for the immune response.

Figure 2:
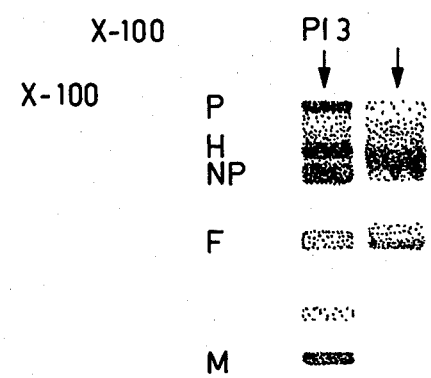
Figure 3:
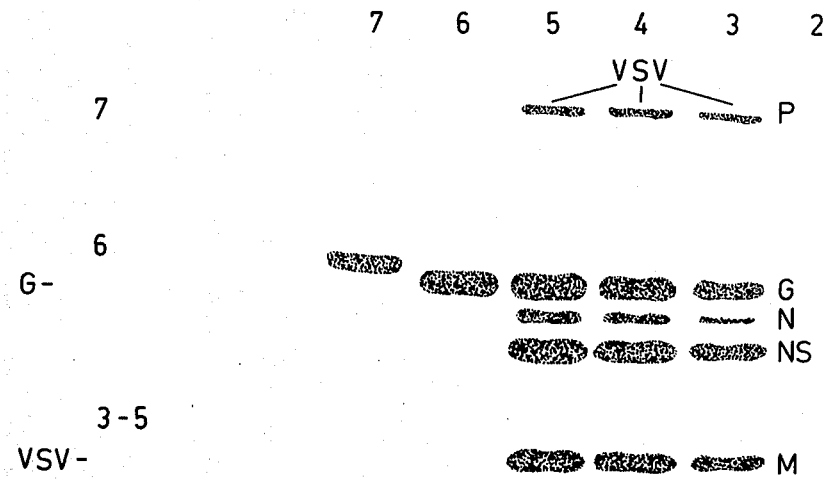

The appended drawing will serve for further explanation. In this drawing,

FIG. 1 is a representation of the arrangement of the layers in accordance with the invention in the centrifuge vessel at the beginning of the centrifugation for Example 1, FIG. 2 is an SDS gel electropherogram of the aggregates (micelles) of Example 1, and FIG. 3 is an SDS gel electropherogram of the aggregates of Example 3.

The activity of a vaccine prepared in accordance with the invention from parainfluenza-3 virus (P 13 virus) was tested on special pathogen-free (SPF) sheep. It is known that it is possible to protect SPF lambs against P 13 virus by vaccination. However, vaccines on the basis of whole viruses alone have proven ineffective (Res. Vet. Sc. 19, 56 [1975]). But if adjuvant is added, protection can be achieved. The vaccine of the invention was tested in SPF lambs, both with and without adjuvant. The control group received no vaccine.

The details of the experiments performed are given in the following Tables 1 and 2.

TABLE 1

| | No. of ani- | Treatment | | |
|---|---|---|---|---|
| | | Weeks following inoculation | | |
| Group | mals | 0 | 3 | 6 | 7 |
| A | 4 | not inoculated | not inoculated | infected with P13 virus, I/N and I/T (G-2/625/6) $10^9$ pfu | lambs killed and autopsied |
| B | 7 | 15 µg of micelles TN buffer i.m. | 15 µg of micelles TN buffer i.m. | infected with P13 virus, I/N and I/T (G-2/625/6) $10^9$ pfu | lambs killed and autopsied |
| C | 6 | 15 µg of micelles Bayol/Falba adjuvant i.m. | 15 µg of micelles TN buffer i.m. | infected with P13 virus, I/N and I/T (G-2/625/6) $10^9$ pfu | lambs killed and autopsied |

The most sensitive test for immunity is the virus discharge from the nose. The results obtained in this case are shown in Table 2.

TABLE 2

| | P-13 Virus Obtained from Nasal Smears | | | | | | | |
|---|---|---|---|---|---|---|---|---|
| Group | 1 | 2 | 3 | 4 | 5 | 6 | 7 | Lungs |
| A | 4/4 | 3/4 | 4/4 | 4/4 | 4/4 | 4/4 | 0/4 | 0/4 |
| B | 7/7 | 6/7 | 7/7 | 7/7 | 5/7 | 0/7 | 0/7 | 0/7 |
| C | 1/6 | 0/6 | 1/6 | 1/6 | 1/6 | 0/6 | 0/6 | 0/6 |

The above results shown that Group C was completely protected. This is supported by the results of the autopsies. No indications whatever of pneumonia could be recognized in this group. In the case of Group B, which had been twice treated with 15 µg of micelle of protein without adjuvant, the animals showed a certain protection. The nasal virus discharge ceased one day sooner than in the controls and the lung lesions were decidedly less severe.

The results of the experiment show that, with the extremely low dose of 15 micrograms of protein, protection can be achieved against massive virus infection ($10^9$ pfu!). On the other hand, in the case of the vaccine of German Offenlegungsschrift No. 2,829,089, for example, an injection of 0.1 to 1 mg of protein was necessary for the achievement of an immune response in mice, and for the achievement of immunity, an additional booster injection was necessary. If the different weight of the animals is compared, it can be seen that the vaccine in accordance with the invention is at least two or three powers of ten more effective.

The following examples will further explain the invention.

EXAMPLE 1

Parainfluenza 3 (P 13) virus (ovine strain, Moredun Institute, Edinburgh, G.B.) was [obtained] from the extracellular medium of primary kidney cell cultures [and] purified by concentration by hollow fiber dialysis and isolation by density gradient centrifugation. The virus was obtained in the form of a tablet-like precipitate in the ultracentrifuge and dissolved in 0.1 M NaCl and 0.05 M tris, pH 7.4.

5 mg of Triton X100 was added to 1 mg of the virus. The solution obtained was layered above a saccharose gradient. The saccharose gradient consisted of a saccharose solution having a saccharose content increasing linearly from 20 to 50% in the same Tris-NaCl buffer as described above. On top of the saccharose gradient was a layer of a 15% solution of saccharose containing 1% of Triton X100 in the same buffer. Then centrifugation was performed for 22 hours at 40,000 rpm on an SW40 Spinko centrifuge (approx. 190,000 g). FIG. 1 of the drawing shows the arrangement of the layers in the centrifuge glass. At the end of the centrifugation, the nucleocapside was found in the precipitate and the spike protein in the center of the gradient. The fractions containing spike protein were combined, dialyzed against 1/10 TN buffer overnight with one replacement of the buffer, and then lyophilized.

Examination of the lyophilizate in the electron microscope disclosed rosette-like structures. The S value of the protein micelles was 32 S. The result of the SDS gel electrophoresis is shown in FIG. 2.

EXAMPLE 2

In a manner similar to that described above, viruses of the myxo group (fowl plague) were used as starting material for the production of the vaccine, with the formation of detergent-free spike protein aggregates. The centrifugation time was 19 hours. The virus was obtained from the Institut für Virologie of the University of Giessen.

EXAMPLE 3

In the manner described in Example 1, vaccine of the rhabdovirus VSV (vesicular stomatitis virus, Animal Virus Research Institute, Pirbright, Woking Surrey, GB) was prepared. However, 0.05 M tris, pH 8, containing 0.2 M NaCl, was used as the buffer. Centrifugation was performed for 24 hours. FIG. 3 shows the result of the SDS gel electrophoresis of the G-protein micelles obtained.

We claim:

1. Process of preparing immunogenically active, lipid- and detergent-free soluble aggregates of amphiphilic membrane proteins of parainfluenza-, influenza- or rhabdo-viruses by extraction of the membrane with surface active agents, which process comprises mixing the virus with a nonionic bile acid detergent, layering the mixture in buffered aqueous salt solution above a detergent-free sugar gradient which in turn is over-layered with a detergent-containing sugar solution, centrifuging the resulting mixture at a centrifugal force of at least 150,000 g, isolating the protein-containing fraction, dialyzing same against the buffered solution, and then lyophilizing the obtained protein micelle solution.

2. Process as claimed in claim 1, wherein the sugar is saccharose.

3. Process as claimed in claim 1 wherein in such sugar gradient the initial concentration is 15 to 25% and the final concentration is 45 to 60%.

4. Process as claimed in claim 1 wherein the virus and detergent are mixed in a weight ratio of 1:3 to 1:10.

5. Process as claimed in claim 1 wherein the aqueous salt solution is 0.05 to 0.2 molar NaCl solution.

6. Process as claimed in claim 1 wherein the pH value of between 6.5 and 8.0 is employed.

7. Process as claimed in claim 1 wherein said protein micelles are dissolved in an adjuvant.

8. Process as claimed in claim 7 wherein said adjuvant in Freund's incomplete adjuvant.

* * * * *